US010034685B2

(12) United States Patent
Boudreaux et al.

(10) Patent No.: US 10,034,685 B2
(45) Date of Patent: Jul. 31, 2018

(54) FEATURES TO APPLY FLUID TO AN ULTRASONIC BLADE OF A SURGICAL INSTRUMENT

(71) Applicant: Ethicon Endo-Surgery, Inc., Cincinnati, OH (US)

(72) Inventors: Chad P. Boudreaux, Cincinnati, OH (US); Jacob S. Gee, Cincinnati, OH (US); David J. Cagle, Cincinnati, OH (US); Jeffrey D. Messerly, Cincinnati, OH (US); William B. Weisenburgh, II, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 542 days.

(21) Appl. No.: 14/552,530

(22) Filed: Nov. 25, 2014

(65) Prior Publication Data
US 2015/0148832 A1 May 28, 2015

Related U.S. Application Data

(60) Provisional application No. 61/908,920, filed on Nov. 26, 2013.

(51) Int. Cl.
A61B 17/32 (2006.01)
A61N 7/00 (2006.01)
(Continued)

(52) U.S. Cl.
CPC ............. *A61B 17/320092* (2013.01); *A61B 17/320068* (2013.01); *A61N 7/00* (2013.01);
(Continued)

(58) Field of Classification Search
CPC .... A61B 17/320068; A61B 17/320092; A61B 2018/0063; A61B 2018/00011; A61B 2017/2829; A61B 2017/320084
See application file for complete search history.

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

CN 101883529 A 11/2010
JP 2014-000311 1/2014
(Continued)

OTHER PUBLICATIONS

U.S. Appl. No. 61/410,603, filed Nov. 5, 2010.
(Continued)

*Primary Examiner* — Anh Dang
(74) *Attorney, Agent, or Firm* — Frost Brown Todd LLC

(57) ABSTRACT

An apparatus comprises a body, a shaft assembly, an end effector, and a wetting member. The shaft assembly extends distally from the body. The end effector is located at a distal end of the shaft assembly. The end effector comprises an ultrasonic blade that is configured to vibrate at an ultrasonic frequency. The wetting member is selectively movable between a first position and a second position. The wetting member is configured to be spaced away from the ultrasonic blade in the first position. The wetting member is configured to contact the ultrasonic blade in the second position and thereby apply a cooling fluid to the ultrasonic blade.

18 Claims, 18 Drawing Sheets

(51) Int. Cl.
  *A61B 18/00* (2006.01)
  *A61B 18/14* (2006.01)
  *A61B 17/00* (2006.01)
  *A61B 17/28* (2006.01)
  *A61B 90/00* (2016.01)

(52) U.S. Cl.
  CPC . *A61B 18/1442* (2013.01); *A61B 2017/00353* (2013.01); *A61B 2017/2825* (2013.01); *A61B 2017/320076* (2013.01); *A61B 2017/320084* (2013.01); *A61B 2018/00011* (2013.01); *A61B 2018/0063* (2013.01); *A61B 2018/00107* (2013.01); *A61B 2090/0436* (2016.02); *A61B 2090/0472* (2016.02)

(56) References Cited

U.S. PATENT DOCUMENTS

| | | | |
|---|---|---|---|
| 5,980,510 | A | 11/1999 | Tsonton et al. |
| 6,056,735 | A | 5/2000 | Okada et al. |
| 6,193,709 | B1 | 2/2001 | Miyawaki et al. |
| 6,325,811 | B1 | 12/2001 | Messerly |
| 6,358,267 | B1 | 3/2002 | Murakami et al. |
| 6,500,176 | B1 | 12/2002 | Truckai et al. |
| 6,669,690 | B1* | 12/2003 | Okada ............ A61B 17/320092 606/169 |
| 6,773,444 | B2 | 8/2004 | Messerly |
| 6,783,524 | B2 | 8/2004 | Anderson et al. |
| 6,958,070 | B2 | 10/2005 | Witt et al. |
| 7,066,936 | B2 | 6/2006 | Ryan |
| 7,074,219 | B2 | 7/2006 | Levine et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,223,267 | B2 | 5/2007 | Isola et al. |
| 7,235,073 | B2 | 6/2007 | Levine et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 7,563,269 | B2 | 7/2009 | Hashiguchi |
| 7,901,423 | B2 | 3/2011 | Stulen et al. |
| 8,057,498 | B2 | 11/2011 | Robertson |
| 8,328,834 | B2 | 12/2012 | Isaacs et al. |
| 8,348,880 | B2 | 1/2013 | Messerly et al. |
| 8,444,663 | B2 | 5/2013 | Houser et al. |
| 8,444,664 | B2 | 5/2013 | Balanev et al. |
| 8,461,744 | B2 | 6/2013 | Wiener et al. |
| 8,523,889 | B2 | 9/2013 | Stulen et al. |
| 8,535,257 | B1* | 9/2013 | Zelten ................ A61B 5/15003 604/1 |
| 8,591,459 | B2 | 11/2013 | Clymer et al. |
| 8,591,536 | B2 | 11/2013 | Robertson |
| 8,623,027 | B2 | 1/2014 | Price et al. |
| 8,652,132 | B2 | 2/2014 | Tsuchiya et al. |
| 8,662,745 | B2 | 3/2014 | Mishuchenko et al. |
| 8,685,020 | B2 | 4/2014 | Weizman et al. |
| 8,974,447 | B2 | 3/2015 | Kimball et al. |
| 8,986,302 | B2 | 3/2015 | Aldridge et al. |
| 9,005,199 | B2 | 4/2015 | Beckman et al. |
| 9,023,071 | B2 | 5/2015 | Miller et al. |
| 9,192,428 | B2 | 11/2015 | Houser et al. |
| 2005/0192611 | A1 | 9/2005 | Houser |
| 2005/0273126 | A1 | 12/2005 | Beaupre |
| 2006/0079874 | A1 | 4/2006 | Faller et al. |
| 2006/0265035 | A1* | 11/2006 | Yachi ............ A61B 17/320092 607/101 |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0030440 | A1 | 1/2009 | Mastri et al. |
| 2009/0036914 | A1 | 2/2009 | Houser |
| 2010/0331873 | A1 | 12/2010 | Dannaher et al. |
| 2012/0112687 | A1 | 5/2012 | Houser et al. |
| 2012/0116265 | A1 | 5/2012 | Houser et al. |
| 2013/0090576 | A1 | 4/2013 | Stulen et al. |
| 2013/0103065 | A1 | 4/2013 | Timm et al. |
| 2013/0303949 | A1 | 11/2013 | Kawaguchi et al. |
| 2014/0005668 | A1 | 1/2014 | Rhee et al. |
| 2014/0005701 | A1 | 1/2014 | Olson et al. |
| 2014/0012297 | A1 | 1/2014 | Ross et al. |
| 2014/0012298 | A1 | 1/2014 | Cunningham et al. |
| 2014/0012299 | A1 | 1/2014 | Stoddard et al. |
| 2014/0114334 | A1 | 4/2014 | Olson et al. |
| 2014/0135804 | A1 | 5/2014 | Weisenburgh et al. |
| 2014/0163549 | A1 | 6/2014 | Yates et al. |
| 2014/0180002 | A1 | 6/2014 | Voic |
| 2015/0080924 | A1 | 3/2015 | Stulen et al. |
| 2015/0080925 | A1 | 3/2015 | Schulte et al. |
| 2015/0122530 | A1 | 5/2015 | Katsuda |
| 2015/0148833 | A1 | 5/2015 | Stokes et al. |
| 2015/0148834 | A1 | 5/2015 | Gee et al. |
| 2015/0148835 | A1 | 5/2015 | Faller et al. |

FOREIGN PATENT DOCUMENTS

| | | |
|---|---|---|
| JP | WO 2013/157571 A1 | 12/2015 |
| WO | WO 2012/116957 | 9/2012 |
| WO | WO 2013/183715 | 12/2013 |
| WO | WO 2013/062103 | 4/2015 |
| WO | WO 2015/081038 A1 | 6/2015 |
| WO | WO 2015/081039 A1 | 6/2015 |
| WO | WO 2015/081040 A1 | 6/2015 |
| WO | WO 2015/081042 A1 | 6/2015 |

OTHER PUBLICATIONS

U.S. Appl. No. 14/553,142, filed Nov. 25, 2014.
U.S. Appl. No. 14/553,378, filed Nov. 25, 2014.
U.S. Appl. No. 14/553,329, filed Nov. 25, 2014.
International Search Report and Written Opinion dated Jan. 30, 2015 for Application No. PCT/US2014/067221, 10 pgs.
International Search Report and Written Opinion dated Feb. 12, 2015 for Application No. PCT/US2014/067218, 9 pgs.
International Search Report and Written Opinion dated Feb. 12, 2015 for Application No. PCT/US2014/067219, 9 pgs.
International Search Report and Written Opinion dated Feb. 12, 2015 for Application No. PCT/US2014/067225, 9 pgs.
U.S. Appl. No. 14/553,142.
U.S. Appl. No. 14/553,329; and.
U.S. Appl. No. 14/553,378.
U.S. Appl. No. 14/552,552.
U.S. Appl. No. 14/552,614.
U.S. Appl. No. 14/552,681.
Search report dated Jan. 15, 2018 for Chinese Patent Application No. 201480073943.5.
Office Action dated Jan. 23, 2018 for Chinese Patent Application No. 201480073943.5.

* cited by examiner

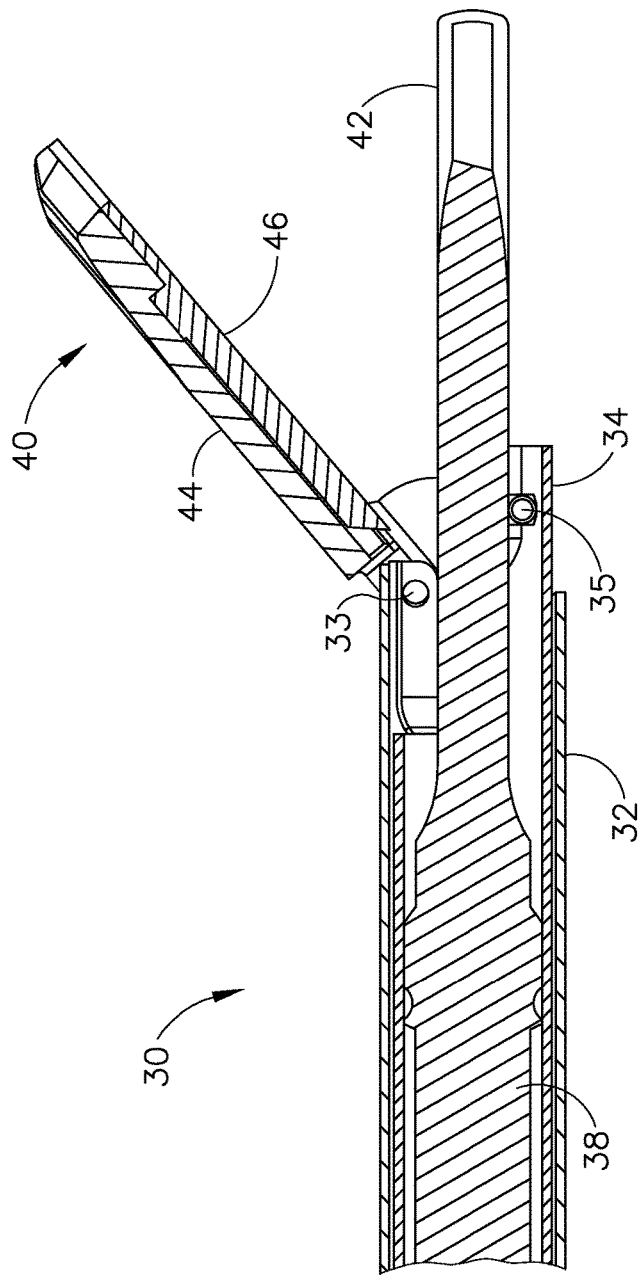

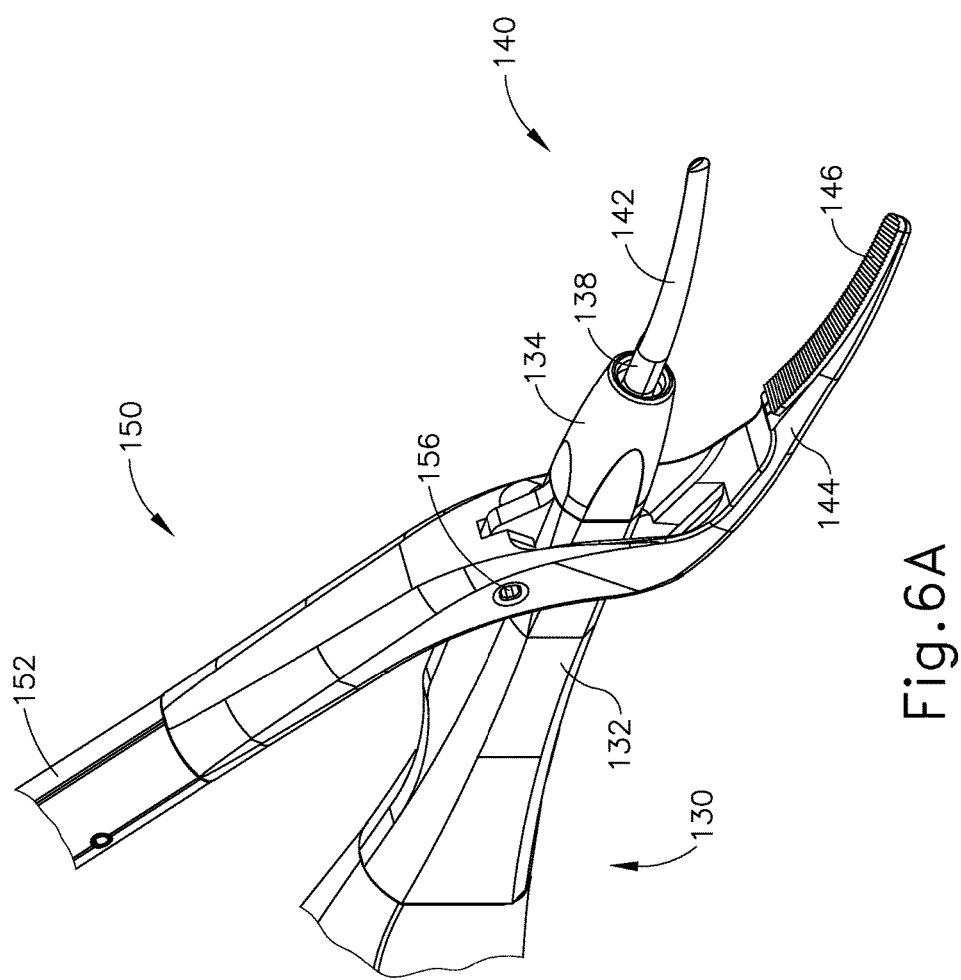

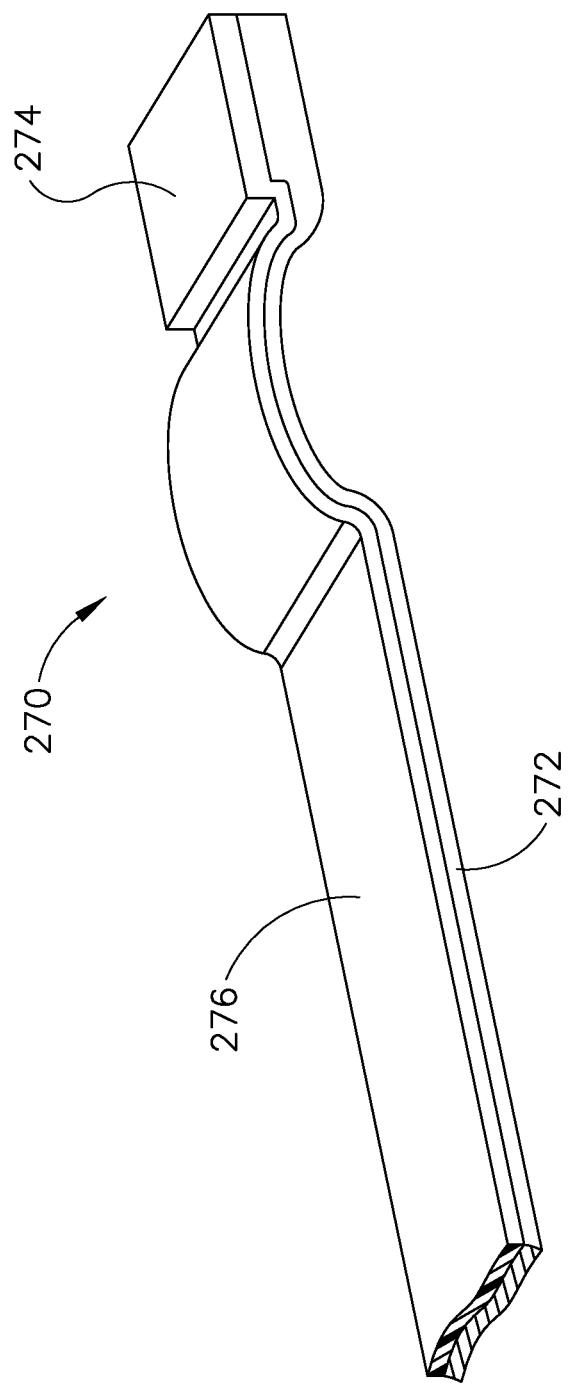

FEATURES TO APPLY FLUID TO AN ULTRASONIC BLADE OF A SURGICAL INSTRUMENT

PRIORITY

This application claims priority to U.S. Provisional Patent App. No. 61/908,920, entitled "Heat Management for Ultrasonic Surgical Instrument," filed Nov. 26, 2013, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, now U.S. Pat. No. 9,393,037, issued Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side cross-sectional view of the end effector of FIG. 2, in the open configuration;

FIG. 6A depicts a perspective view of the end effector of FIG. 5, in an open configuration;

FIG. 8 depicts a perspective view of the cooling element of FIG. 7A;

Figure 1:
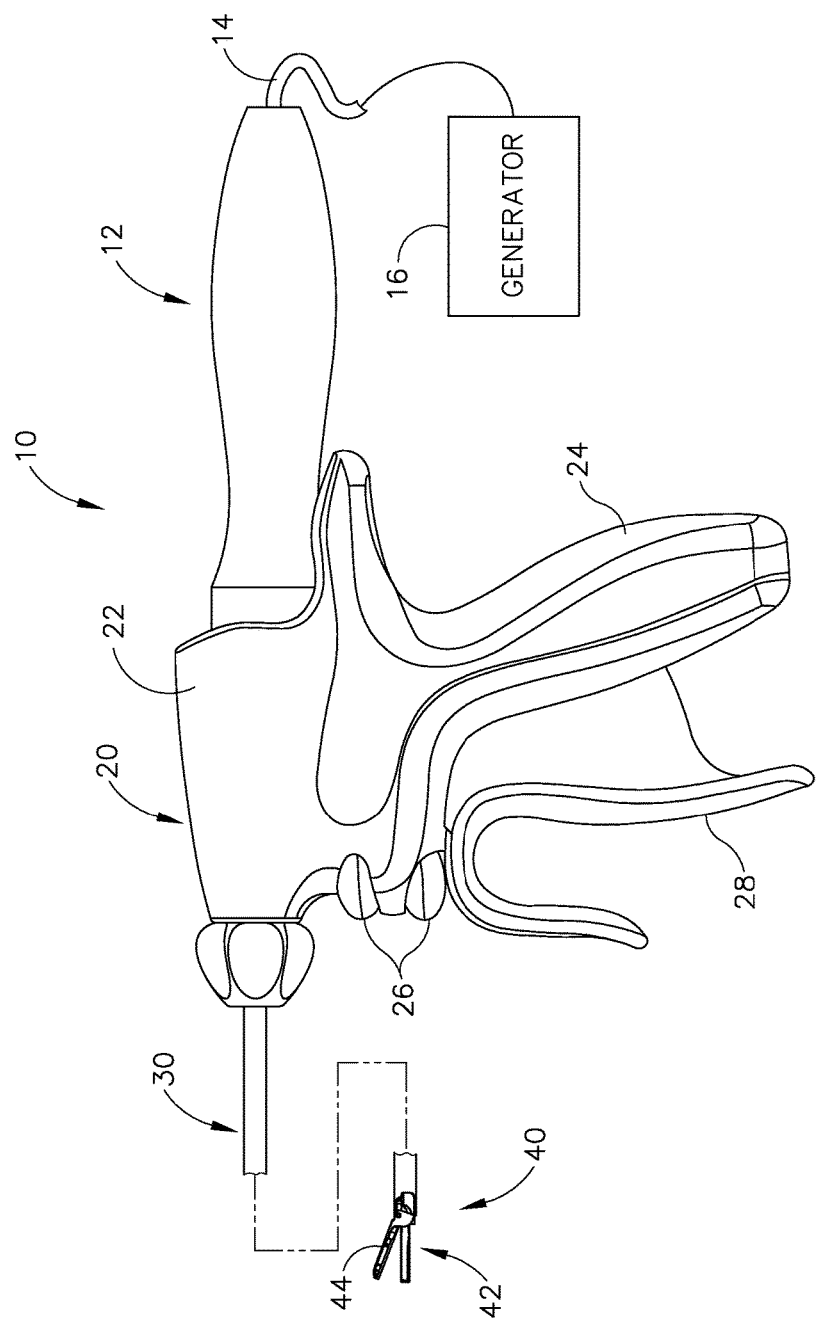
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6B illustrate exemplary ultrasonic surgical instruments (10, 100). At least part of each instrument (10, 100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, now U.S. Pat. No. 8,623,027; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; U.S. Pub. No. 2014/0114334, now U.S. Pat. No. 9,095,367; U.S. Pat. App. No. 61/410,603; and/or U.S. patent application Ser. No. 14/028,717, published as U.S. Pub. No. 2015/0080924 on Mar. 19, 2015. The disclosures of each of the foregoing patents, publications, and applications are incorporated by reference herein. As described therein and as will be described in greater detail below, each instrument (10, 100) is operable to cut tissue and seal or weld tissue (e.g., a blood vessel, etc.) substantially simultaneously. It should also be understood that instruments (10, 100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (10, 100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (10, 100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
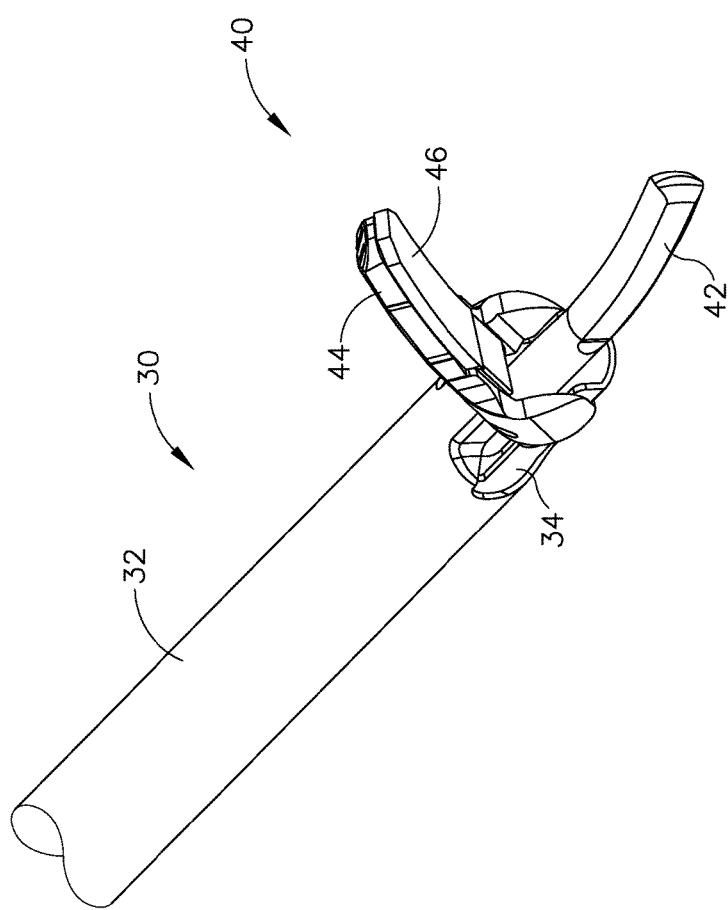
FIG. 2 depicts a perspective view of the end effector of the instrument of FIG. 1, in an open configuration.
Figure 3B:
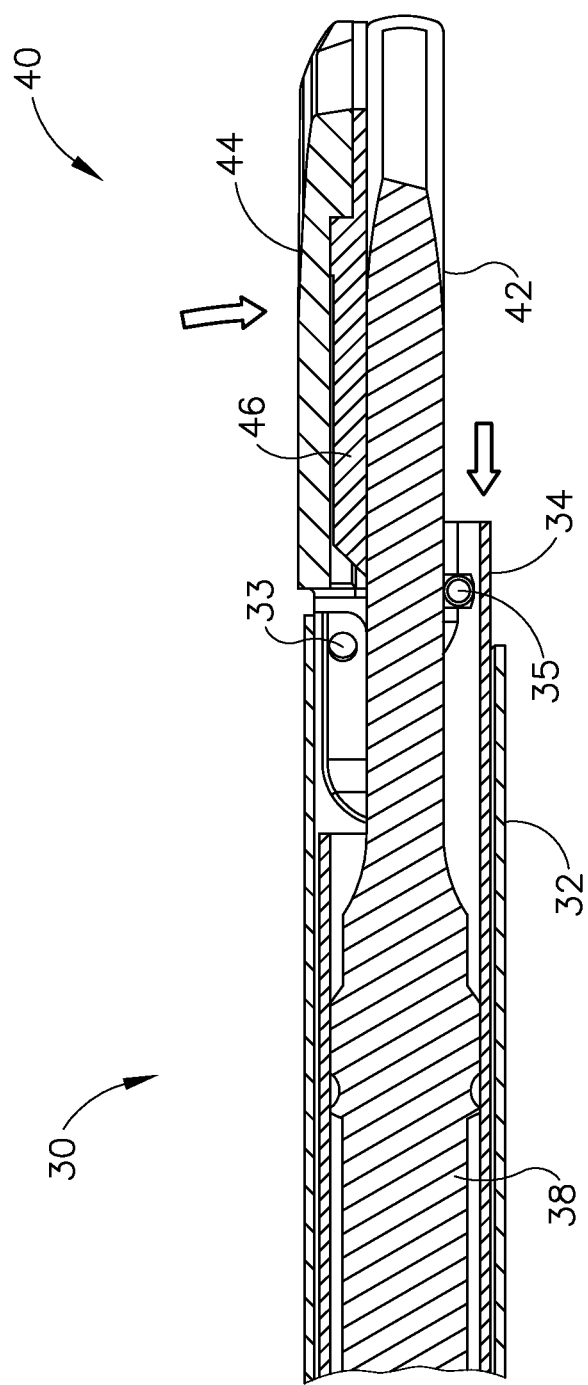
FIG. 3B depicts a side cross-sectional view of the end effector of FIG. 2, in a closed configuration.

A. Exemplary Ultrasonic Surgical Instrument for Minimally Invasive Surgical Procedures FIG. 1 illustrates an exemplary ultrasonic surgical instrument (10) that is configured to be used in minimally invasive surgical procedures (e.g., via a trocar or other small diameter access port, etc.). Instrument (10) of this example comprises a handle assembly (20), a shaft assembly (30), and an end effector (40). As shown in FIGS. 2-3B, shaft assembly (30) comprises an outer sheath (32), an inner tube (34) slidably disposed within outer sheath (32), and a waveguide (38) disposed within inner tube (34). As will be discussed in more detail below, longitudinal translation of inner tube (34) relative to outer sheath (32) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. In the present example, a resilient member biases trigger (28) away from pistol grip (24). Trigger (28) is pivotable toward pistol grip (24) to drive inner tube (34) proximally relative to outer sheath (32). When trigger (28) is thereafter released or driven away from pistol grip (24), inner tube (34) is driven distally relative to outer sheath (32). By way of example only, trigger (28) may be coupled with inner tube (34) in accordance with the teachings of various references cited herein. Other suitable ways in which trigger (28) may be coupled with inner tube (34) will be apparent to those of ordinary skill in the art in view of the teachings herein.

As shown in FIGS. 2-3B, end effector (40) includes an ultrasonic blade (42) and a pivoting clamp arm (44). Clamp arm (44) includes a clamp pad (46) facing ultrasonic blade (42). Clamp arm (44) is pivotably coupled with a distal end of outer sheath (32) of shaft assembly (30), above ultrasonic blade (42), via a pin (33). A distal end of inner tube (34) is pivotably coupled with a proximal end of clamp arm (44), below ultrasonic blade (42), via another pin (35). Thus, longitudinal translation of inner tube (34) relative to outer sheath (32) causes clamp arm (44) to pivot about pin (33) toward and away from ultrasonic blade (42) to thereby clamp tissue between clamp pad (46) and ultrasonic blade (42) to transect and/or seal the tissue. In particular, as seen in the transition from FIGS. 3A to FIG. 3B, proximal longitudinal translation of inner tube (34) relative to outer sheath (32) and handle assembly (20) causes clamp arm (44) to pivot toward ultrasonic blade (42); and distal longitudinal translation of inner tube (34) relative to outer sheath (32) and handle assembly (20) causes clamp arm (44) to pivot away from ultrasonic blade (42). It should therefore be understood that pivoting of trigger (28) toward pistol grip (24) will cause clamp arm (44) to pivot toward ultrasonic blade (42); and that pivoting of trigger (28) away from pistol grip (24) will cause clamp arm (44) to pivot away from ultrasonic blade (42).

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (38), which extends through shaft assembly (30) to reach ultrasonic blade (42). Waveguide (38) is secured within shaft assembly (30) via a pin (not shown), which passes through waveguide (38) and shaft assembly (30). This pin is located at a position along the length of waveguide (38) corresponding to a node associated with resonant ultrasonic vibrations communicated through waveguide (38). As noted above, when ultrasonic blade (42) is in an activated state (i.e., vibrating ultrasonically), ultrasonic blade (42) is operable to effectively cut through and seal tissue, particularly when the tissue is being clamped between clamp pad (46) and ultrasonic blade (42). It should be understood that waveguide (38) may be configured to amplify mechanical vibrations transmitted through waveguide (38). Furthermore, waveguide (38) may include features operable to control the gain of the longitudinal vibrations along waveguide (38) and/or features to tune waveguide (38) to the resonant frequency of the system.

In the present example, the distal end of ultrasonic blade (42) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (42) and clamp pad (46), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and/or clamp pad (46) to also seal the tissue.

An operator may activate buttons (26) to selectively activate transducer assembly (12) to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; and/or U.S. Pub. No. 2014/0114334, now U.S. Pat. No. 9,095,367. Additional merely illustrative variations for instrument (10) will be described in greater detail below. It should be understood that the below described variations may be readily applied to instrument (10) described above and any of the instruments referred to in any of the references that are cited herein, among others.

B. Exemplary Ultrasonic Surgical Instrument for Open Surgical Procedures

Figure 4:
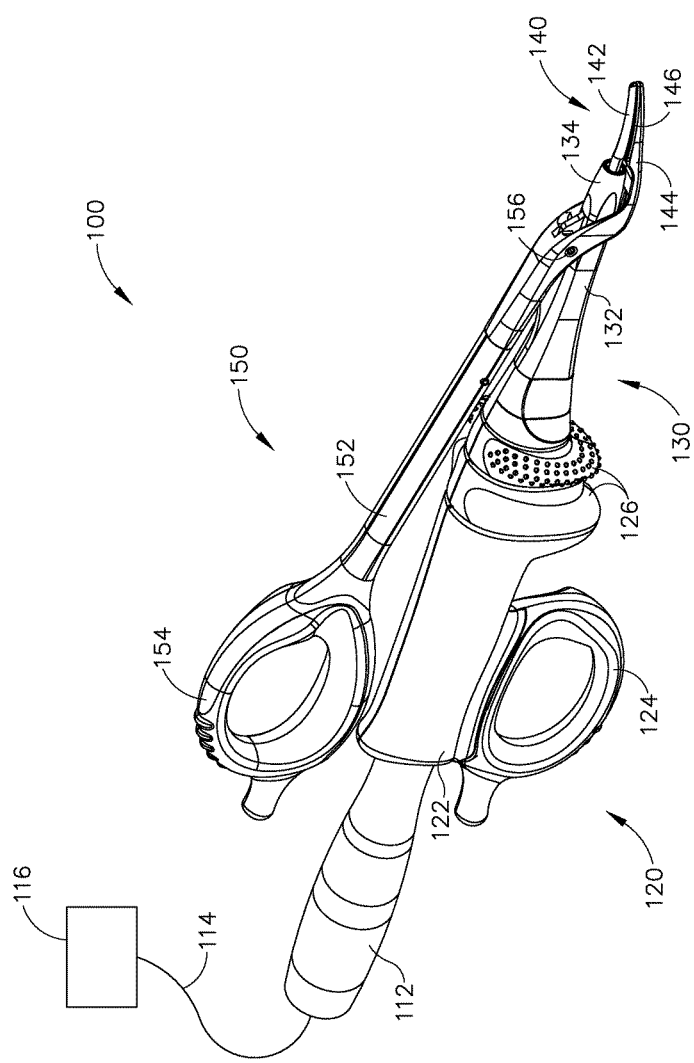
FIG. 4 depicts a perspective view of another exemplary surgical instrument.

FIG. 4 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 5:
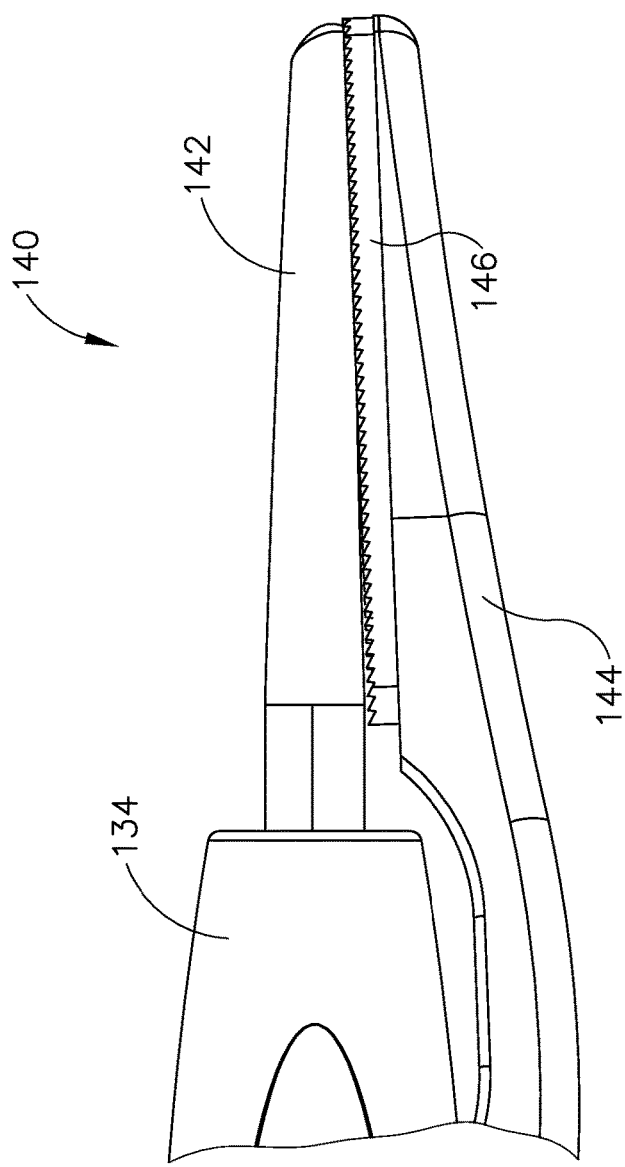
FIG. 5 depicts a side elevational view of the end effector of the instrument of FIG. 4, in a closed configuration.
Figure 6B:
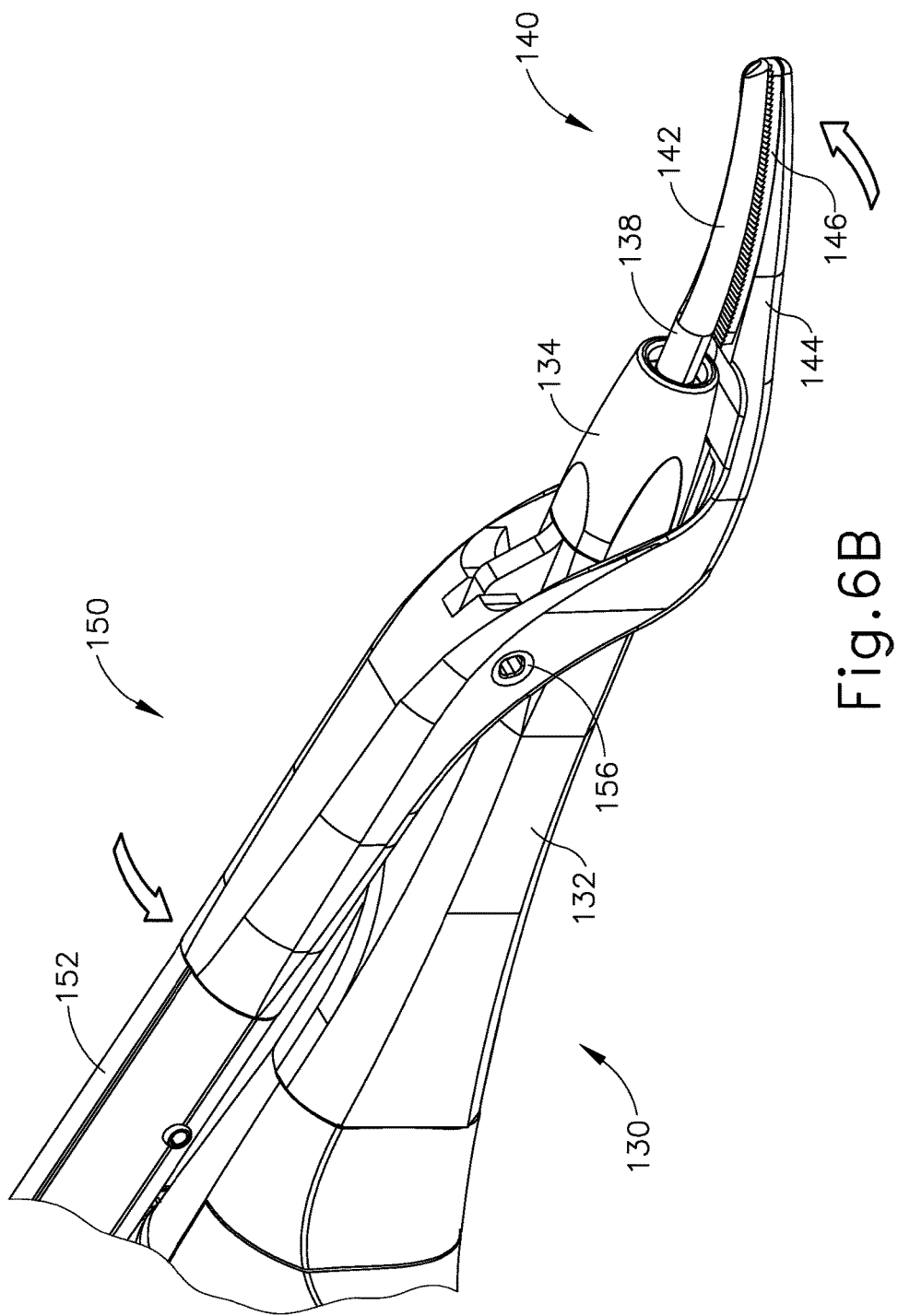
FIG. 6B depicts a perspective view of the end effector of FIG. 5, in a closed configuration.

Shaft assembly (130) comprises an outer sheath (132) extending distally from body (122). A cap (134) is secured to the distal end of sheath (132). As best seen in FIGS. 5-6B, end effector (140) comprises an ultrasonic blade (142) and a clamp arm (144). Ultrasonic blade (142) extends distally from cap (134). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 6A-6B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 6A. By way of example only, such a resilient member may comprise a leaf spring, a torsion spring, and/or any other suitable kind of resilient member.

Referring back to FIG. 4, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126)

are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; U.S. Pub. No. 2014/0114334, now U.S. Pat. No. 9,095,367; and/or U.S. patent application Ser. No. 14/031,665, published as U.S. Pub. No. 2015/0080925 on Mar. 19, 2015. Additional merely illustrative variations for instrument (100) will be described in greater detail below. It should be understood that the below described variations may be readily applied to instrument (100) described above and any of the instruments referred to in any of the references that are cited herein, among others.

II. Exemplary Features for Providing Heat Management in an Ultrasonic Surgical Instrument In some instances, one or more regions of instrument (10, 100) may heat up during extended operation of instrument (10, 100) in a surgical procedure. By way of example only, blade (42, 142), clamp arm (44, 144), and/or other portions of instrument (10, 100) may eventually heat up over time. Such heating may be caused by friction and/or other factors. To the extent that the heat is initially generated in one particular component of instrument (10, 100) (e.g., blade (42, 142) or clamp arm (44, 144), etc.), such heat may be gradually transmitted to other portions of instrument (10, 100). It may be desirable to minimize such heating and/or otherwise manage such heating in order to avoid having heated portions of instrument (10, 100) contact tissue that should not be heated. For instance, the operator may wish for end effector (40, 140) to be relatively cool when the operator wishes to use end effector (40, 140) to perform spreading blunt dissections and/or simple tissue grasping, etc. It may also be desirable to minimize heat and/or otherwise manage heat in a way that does not significantly increase the size or operability of instrument (10, 100). Several examples of how heating may be minimized and/or otherwise managed are described in greater detail below; while other examples will be apparent to those of ordinary skill in the art in view of the teachings herein.

In addition to the examples described below, it should be understood that one or more portions of instrument (10, 100) may include a thermal insulator or barrier coating (e.g., a thin coating of thermal insulator or barrier material with a very low thermal conductivity). An example of a thermal insulator or barrier coating is a nanocomposite (e.g., hydro-NM-oxide) in an acrylic resin suspension. An example of such a coating is NANSULATE® coating by Industrial Nanotech, Inc. of Naples, Florida. Additional merely illustrative examples of thermal insulator or barrier coatings include the following: EST 1711 by Ellison Surface Technologies, Inc. of Mason, Ohio; EST 1732 by Ellison Surface Technologies, Inc. of Mason, Ohio; EST 3030 by Ellison Surface Technologies, Inc. of Mason, Ohio; EST 1711+EST 3030 by Ellison Surface Technologies, Inc. of Mason, Ohio; Oxytech V by Techmetals, Inc. of Dayton, Ohio; Alumina Titania; Zirconium Oxide; Aluminum Oxide; and/or various other kinds of coatings, including combinations thereof.

A thermal insulator or barrier coating may be applied to various external surfaces of instrument (10, 100), such as regions of blade (42, 142) that are not intended to contact tissue, clamp arm (44, 144), clamp pad (46, 146), outer sheath (32, 132), cap (134), etc. In addition or in the alternative, such a coating may be applied to various internal surfaces of instrument (10, 100), such as surfaces in generator (16, 116), transducer assembly (12, 112), internal electronics components, etc. In addition to providing a thermal barrier or insulation, such a coating may serve as a corrosion barrier, fire block, etc. In the below examples that include various components that are added to or otherwise incorporated into variations of instrument (10, 100), the coating may also be applied to one or more regions of such components. Other suitable ways in which a thermal coating may be incorporated into instrument (10, 100) and variations thereof will be apparent to those of ordinary skill in the art in view of the teachings herein.

To the extent that any of the examples discussed below are shown and described in the context of a variation of one particular kind of instrument (10 or 100), it should be understood that the same teachings may be readily applied to the other kind of instrument (10 or 100). Each example described below should therefore not be viewed as only having applicability to either instrument (10) or instrument (100). Furthermore, it is contemplated that the teachings below may be readily applied to other kinds of instruments, not just variations of instruments (10, 100).

One merely exemplary way in which heat may be managed in instrument (10, 100) is to use a fluid to cool blade (42, 142). For instance, a cooling liquid (e.g., saline, etc.) may be applied to the proximal end of blade (42, 142). The cooling fluid may then be communicated distally along the rest of the length of blade (42, 142) to thereby cool blade. The ultrasonic vibration of blade (42, 142) may provide such distal communication of the fluid. In some such versions, a particular vibrational scheme may be used to drive liquid distally along blade (42, 142). Such a particular, vibrational scheme may have no meaningful effect on tissue that is in contact with blade (42, 142) while blade is being driven in such a fashion. For instance, blade (42, 142) may be vibrated in short pulses (e.g., of approximately 10 to 20 millisecond duration) of low amplitude motion to drive the liquid distally along blade (42, 142). In some such instances, generator (16, 116) is programmed to provide such liquid driving ultrasonic activation of blade (42, 142) when the operator is not pressing any buttons (26, 126). In addition or in the alternative, generator (16, 116) may be programmed to provide liquid driving ultrasonic activation of blade (42, 142) when generator (16, 116) detects that blade (42, 142) is not contacting tissue. As yet another merely illustrative example, instrument (10, 100) may include a separate user input feature that is operable to manually trigger a liquid driving vibrational scheme. Other suitable ways in which a liquid driving vibrational scheme may be triggered will be apparent to those of ordinary skill in the art in view of the teachings herein.

In some other versions, the same vibrational movement that is used to drive blade during tissue cutting/sealing may drive liquid distally along blade (42, 142). As yet another merely illustrative example, fluid may be communicated to and/or along blade in accordance with at least some of the teachings of U.S. Pub. No. 2011/0152759, entitled "Use of Biomarkers and Therapeutic Agents with Surgical Devices," published Jun. 23, 2011, now U.S. Pat. No. 8,591,459, issued Nov. 26, 2013, the disclosure of which is incorporated by reference herein. It should be understood that the teachings in U.S. Pub. No. 2011/0152759, now U.S. Pat. No. 8,591,459, issued Nov. 26, 2013, relating to dispensation of medical fluids may be readily adapted to provide communication of cooling fluid. Additional examples of ways in which fluid may be used to cool blade (42, 142) are described in greater detail below; while still further examples will be apparent to those of ordinary skill in the art in view of the teachings herein. It should also be understood that the below teachings may be readily combined with the teachings of U.S. Pub. No. 2016/0143657, entitled "Features for Communication of Fluid through Shaft Assembly of Ultrasonic Surgical Instrument," published May 26, 2016, the disclosure of which is incorporated by reference herein; U.S. Pub. No. 2016/0143659, entitled "Ultrasonic Surgical Instrument with Blade Cooling through Retraction," published May 26, 2016, the disclosure of which is incorporated by reference herein; and U.S. Pub. No. 2016/0143658, entitled "Features to Drive Fluid toward an Ultrasonic Blade of a Surgical Instrument," published May 26, 2016, the disclosure of which is incorporated by reference herein.

A. Exemplary Cantilevered Absorbent Cooling Pad

Figure 7A:
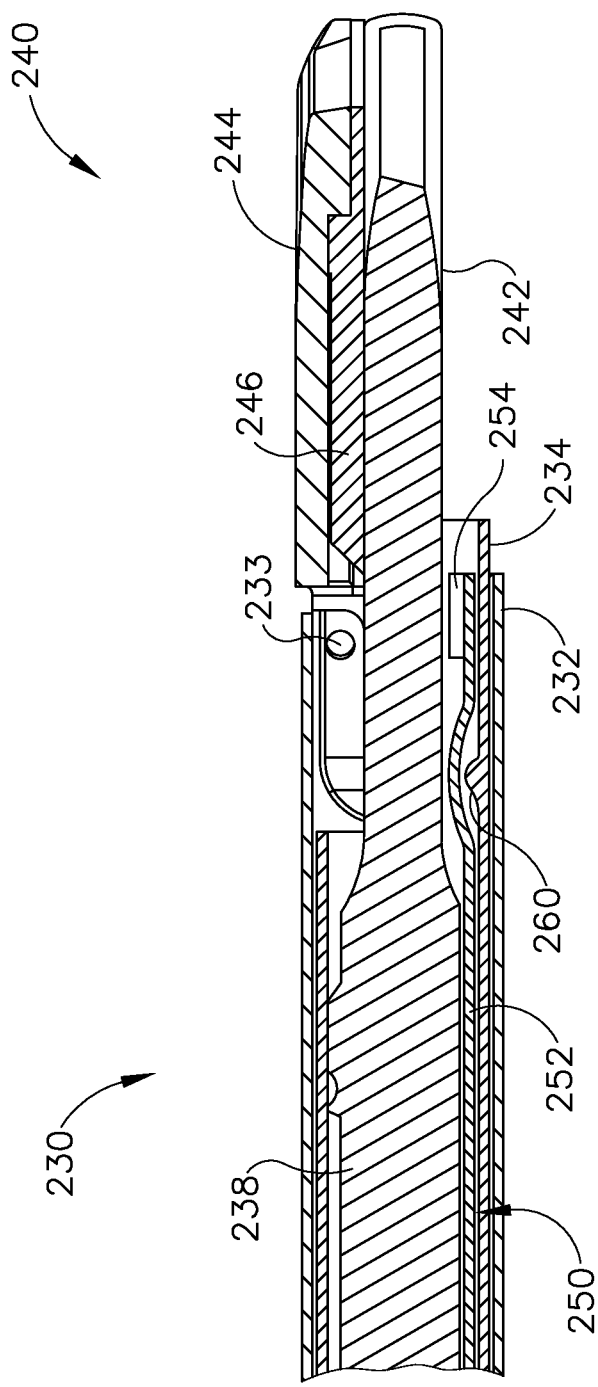
FIG. 7A depicts a cross-sectional side view of an exemplary alternative end effector, in a closed configuration, with a cooling element spaced away from the waveguide.
Figure 7B:
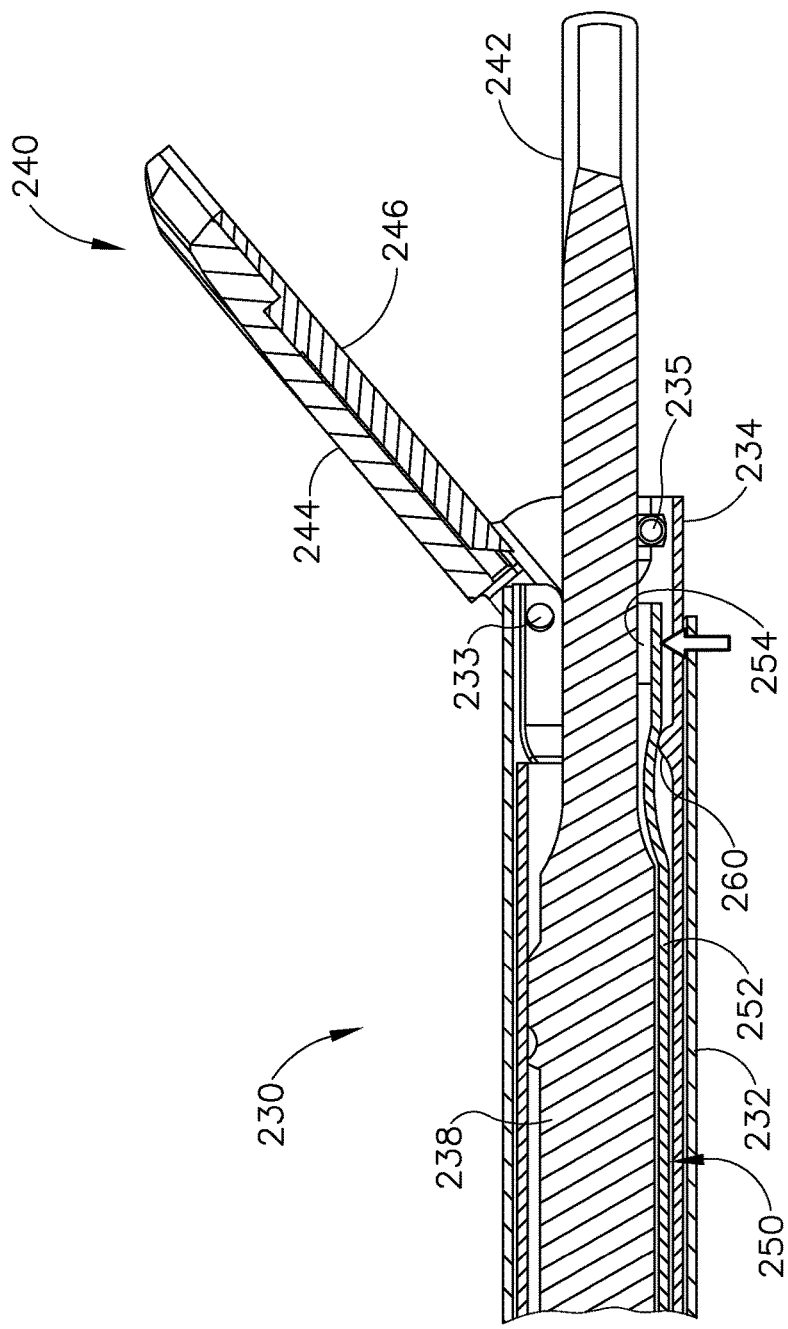
FIG. 7B depicts a cross-sectional side view of the end effector of FIG. 7A, in an open configuration, with the cooling element in contact with the waveguide.

FIGS. 7A-7B show an exemplary alternative end effector (240) positioned at the distal end of an exemplary alternative shaft assembly (230). End effector (240) of this example is substantially identical to end effector (40) described above. In particular, end effector (240) includes an ultrasonic blade (242) and a pivoting clamp arm (244) with clamp pad (246). Shaft assembly (230) is substantially similar to shaft assembly (30) described above. In particular, shaft assembly (230) includes an outer sheath (232) and an inner tube (234). Outer sheath (232) is pivotably coupled with clamp arm (244) via a pin (233); while inner tube (234) is pivotably coupled with clamp arm (244) via a pin (235). Inner tube (234) translates relative to outer sheath (232) to selectively pivot clamp arm (244) toward (FIG. 7A) and away from (FIG. 7B) blade (242). Unlike inner tube (34), however, inner tube (234) of this example includes an inwardly directed protrusion (260). Protrusion (260) is configured to engage a cooling feature (250).

Cooling feature (250) is disposed between waveguide (238) and inner tube (234). Cooling feature (250) includes a cantilever beam (252), which is mechanically grounded relative to outer sheath (232). Inner tube (234) thus translates relative to cantilever beam (252) when inner tube (234) translates relative to outer sheath (232). A hydrophilic pad (254) is located at the distal end of cantilever beam (252). By way of example only, pad (254) may comprise a foam material. Various suitable material(s) that may be used to form pad (254) will be apparent to those of ordinary skill in the art in view of the teachings herein. As seen in the transition from FIG. 7A to FIG. 7B, protrusion (260) of inner tube (234) is configured to drive pad (254) into engagement with the proximal end of blade (242) each time inner tube (234) translates distally relative to cantilever beam (252) and outer sheath (232). This occurs due to a camming engagement by protrusion (260) against the underside of cantilever beam (252). Cantilever beam (252) is bent such that protrusion (260) disengages the underside of cantilever beam (252) when inner tube (234) returns to a proximal position relative to cantilever beam (252) and outer sheath (232). Cantilever beam (252) is resiliently biased to disengage pad (254) from the proximal end of blade (242) when protrusion (260) is disengaged from the underside of cantilever beam (252).

In the present example, pad (254) is saturated in a cooling fluid, such that pad (254) applies the cooling fluid to blade (242) when pad (254) engages blade (242). The saturated pad (254) may thereby quench or otherwise cool blade (242) each time clamp arm (244) is pivoted away from blade (242). By way of example only, the operator may dip end effector (240) and the distal end of shaft assembly (230) into a container holding saline or some other cooling fluid in order to saturate or otherwise wet pad (254). This may be done at the beginning of a surgical procedure and/or during a surgical procedure. FIG. 8 shows an exemplary alternative cooling feature (270) that comprises a cantilever beam (272), a hydrophilic pad (274), and a wicking feature (276) extending proximally from hydrophilic pad (274) along an upper side of cantilever beam (272). Wicking feature (276) is in fluid communication with pad (274) such that fluid absorbed by pad (274) may be wicked into wicking feature (276) by a capillary action. When pad (274) starts to dry out (e.g., after engaging a warm blade (242) one or more times, etc.), fluid in wicking feature (276) may be drawn back into pad (274) through a capillary action.

As yet another merely illustrative variation, a fluid conduit may be coupled with wicking feature (276) and/or pad (254, 274) to communicate fluid directly to wicking feature (276) and/or pad (254, 274) from a source external to the patient (e.g., a reservoir within a handle assembly, etc.). In such versions, wicking feature (276) and/or pad (254, 274) may be replenished with fluid during a surgical procedure without having to remove end effector (240) from the patient. It should also be understood that steam may be generated at the surgical site when blade (242) cuts and seals tissue. Wicking feature (276) and/or pad (254, 274) may absorb fluid from such steam during the surgical procedure. The same concept may also apply to any other absorbent pad described herein.

While cantilever beams (252, 272) and pads (254, 274) are shown as being generally flat in the present example, it should be understood that cantilever beams (252, 272) and pads (254, 274) may instead have a curved profile to complement the curvature of waveguide (238), blade (242), and inner tube (234). As another merely illustrative variation, pad (254, 274) may contact waveguide (238) instead of contacting blade (242). Still other suitable variations will be apparent to those of ordinary skill in the art in view of the teachings herein.

B. Exemplary Cooling Pad Insert for Clamp Arm

Figure 9:
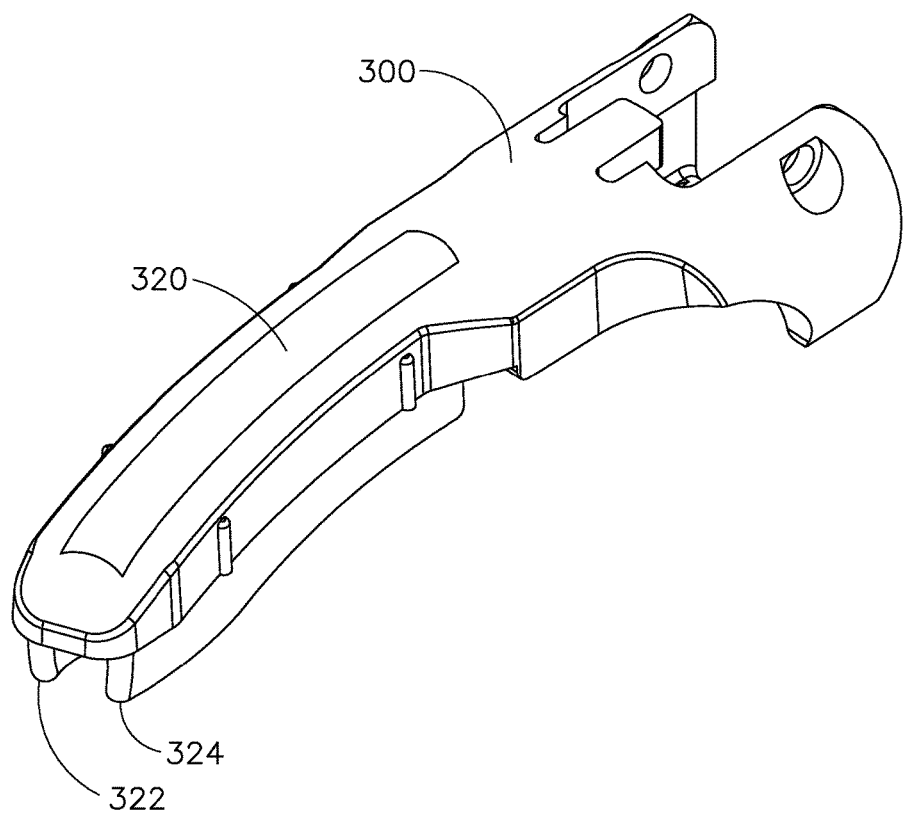
FIG. 9 depicts a perspective view of an exemplary alternative clamp arm.
Figure 10:
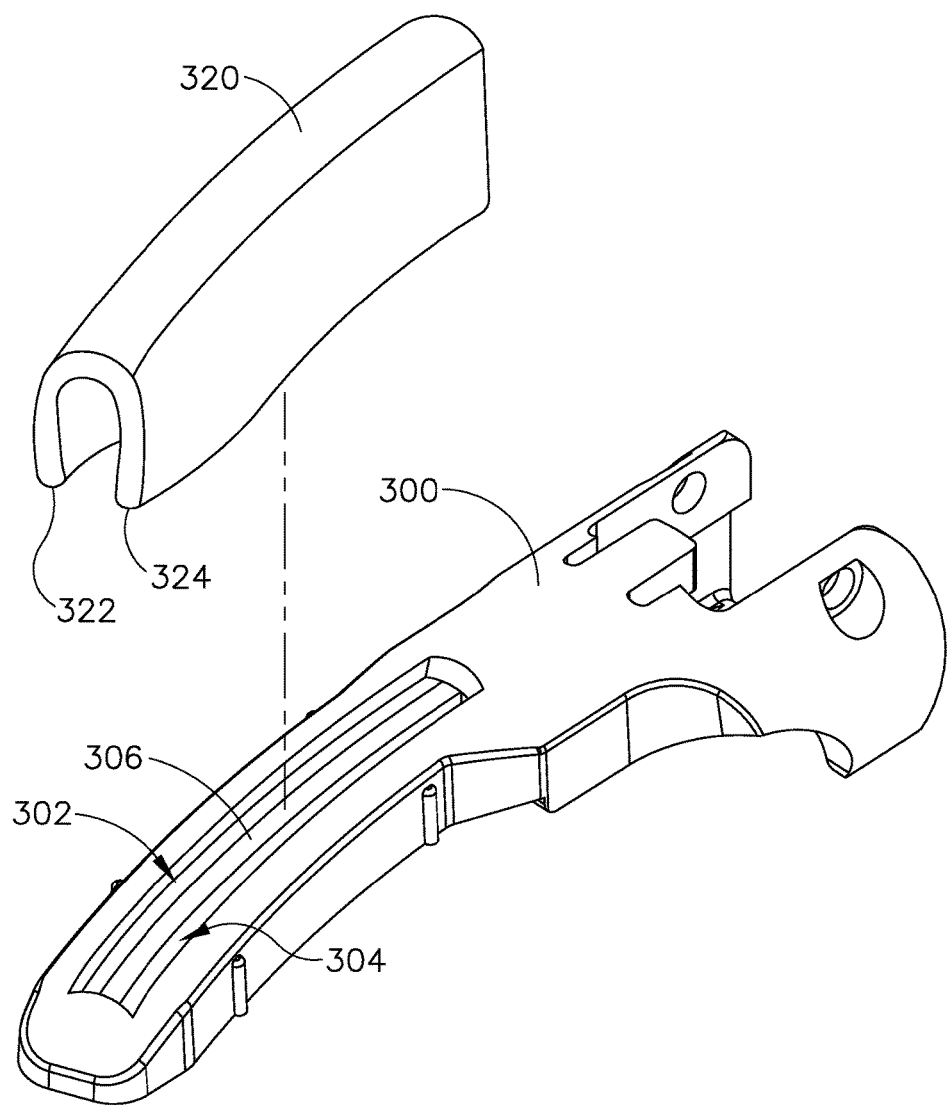
FIG. 10 depicts an exploded view of the clamp arm of FIG. 9.
Figure 11:
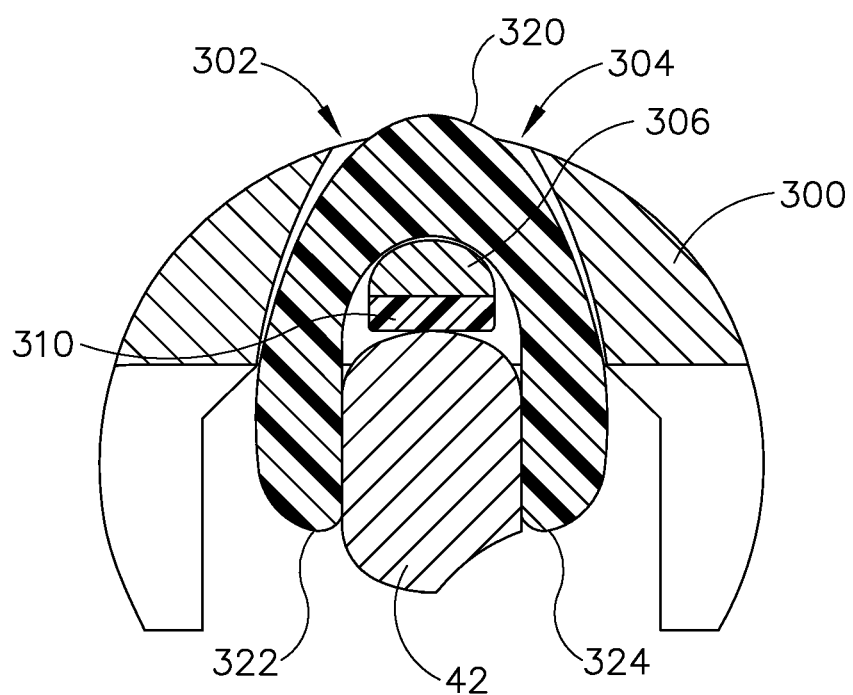
FIG. 11 depicts a cross-sectional end view of the clamp arm of FIG. 9, clamped against an ultrasonic blade.

FIGS. 9-11 show an exemplary alternative clamp arm (300) that may be used as a substitute for clamp arm (44). Clamp arm (300) of this example includes a longitudinally extending support beam (306), a clamp pad (310), and a cooling pad (320). Clamp pad (310) is secured to the underside of support beam (306). Cooling pad (320) is insertable through two channels (302, 304) formed in clamp arm (300) on opposite sides of support beam (306). In particular, cooling pad (320) may be bent to form an upside-down "U" shape; and may then be draped over a support beam (306) defined by clamp arm (300). Cooling pad (320) may remain in place due to friction. With cooling pad (320) secured to clamp arm (300), free ends (322, 324) of cooling pad (320) extend below clamp arm (300) and below clamp pad (310). By way of example only, pad (320) may comprise a foam material. Various suitable material(s) that may be used to form pad (320) will be apparent to those of ordinary skill in the art in view of the teachings herein.

As best seen in FIG. 11, free ends (322, 324) drape over the sides of blade (42) when clamp arm (300) is in a closed position relative to blade (42). Free ends (322, 324) define a gap distance that is less the width of blade (42), such that free ends (322, 324) bear inwardly against the outer surfaces of blade (42) when clamp arm (300) is in a closed position relative to blade (42) as shown in FIG. 11. It should be understood that, during use of clamp arm (300) in a surgical procedure, tissue may initially be captured between clamp arm (300) and blade (42) such that the tissue is interposed between pad (320) and blade (42). Clamp pad (310) and blade (42) may cooperate to sever and seal the tissue, which may then separate from blade (42). Once the tissue is no longer interposed between pad (320) and blade (42), pad (320) may directly engage blade (42) as shown in FIG. 11. It should therefore be understood that pad (320) may engage blade (42) as shown in FIG. 11 right after blade (42) has severed and sealed tissue captured between clamp pad (310) and blade (42).

Pad (320) of this example may be used similar to pad (254, 274) described above. In particular, pad (320) may be saturated or otherwise wetted with a cooling fluid (e.g., saline, etc.). Pad (320) may thus apply the cooling fluid to blade (42) when pad (320) engages blade (42), such that the saturated pad (320) quenches or otherwise cools blade (42) each time clamp arm (300) reaches a closed position relative to blade (42). An end effector that is fitted with clamp arm (300) may be dipped into a container holding saline or some other cooling fluid in order to saturate or otherwise wet pad (320). This may be done at the beginning of a surgical procedure and/or during a surgical procedure. In addition or in the alternative, pad (320) may absorb fluid from vapor emitted by tissue during a surgical procedure and/or other fluid from a surgical site. As yet another merely illustrative variation, a fluid conduit may be coupled with pad (320) to communicate fluid directly to pad (320) from a source external to the patient (e.g., a reservoir within a handle assembly, etc.). Other suitable ways in which pad (320) may be saturated or otherwise wetted will be apparent to those of ordinary skill in the art in view of the teachings herein.

Figure 12:
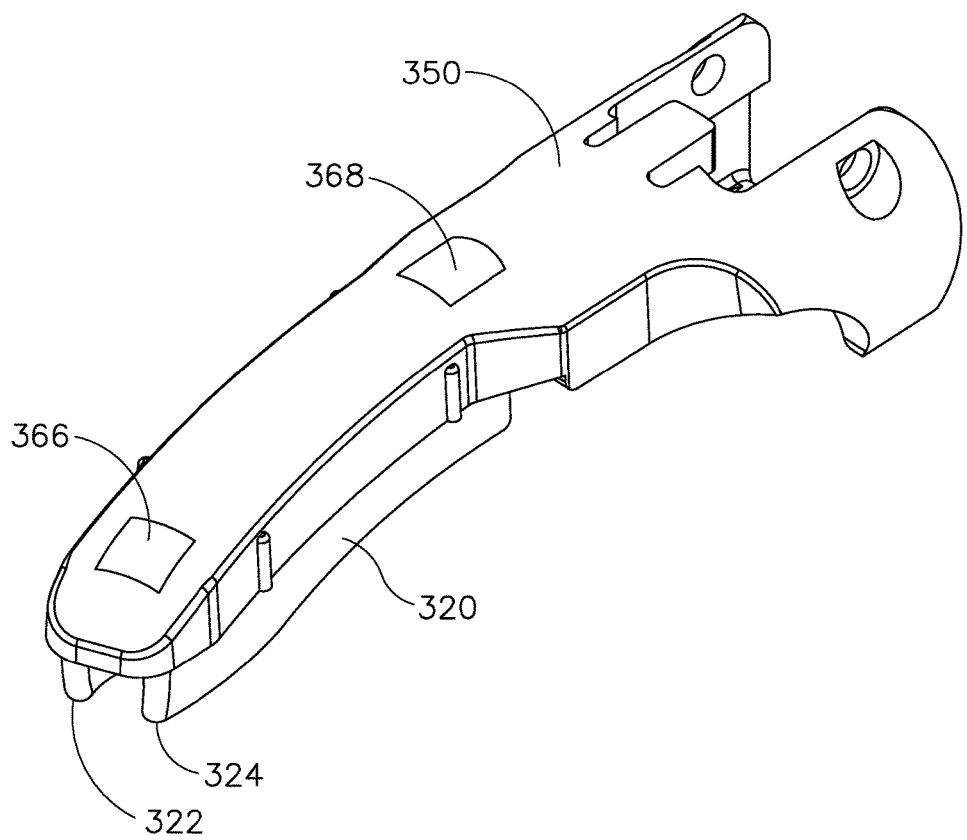
FIG. 12 depicts a perspective view of another exemplary alternative clamp arm.
Figure 13:
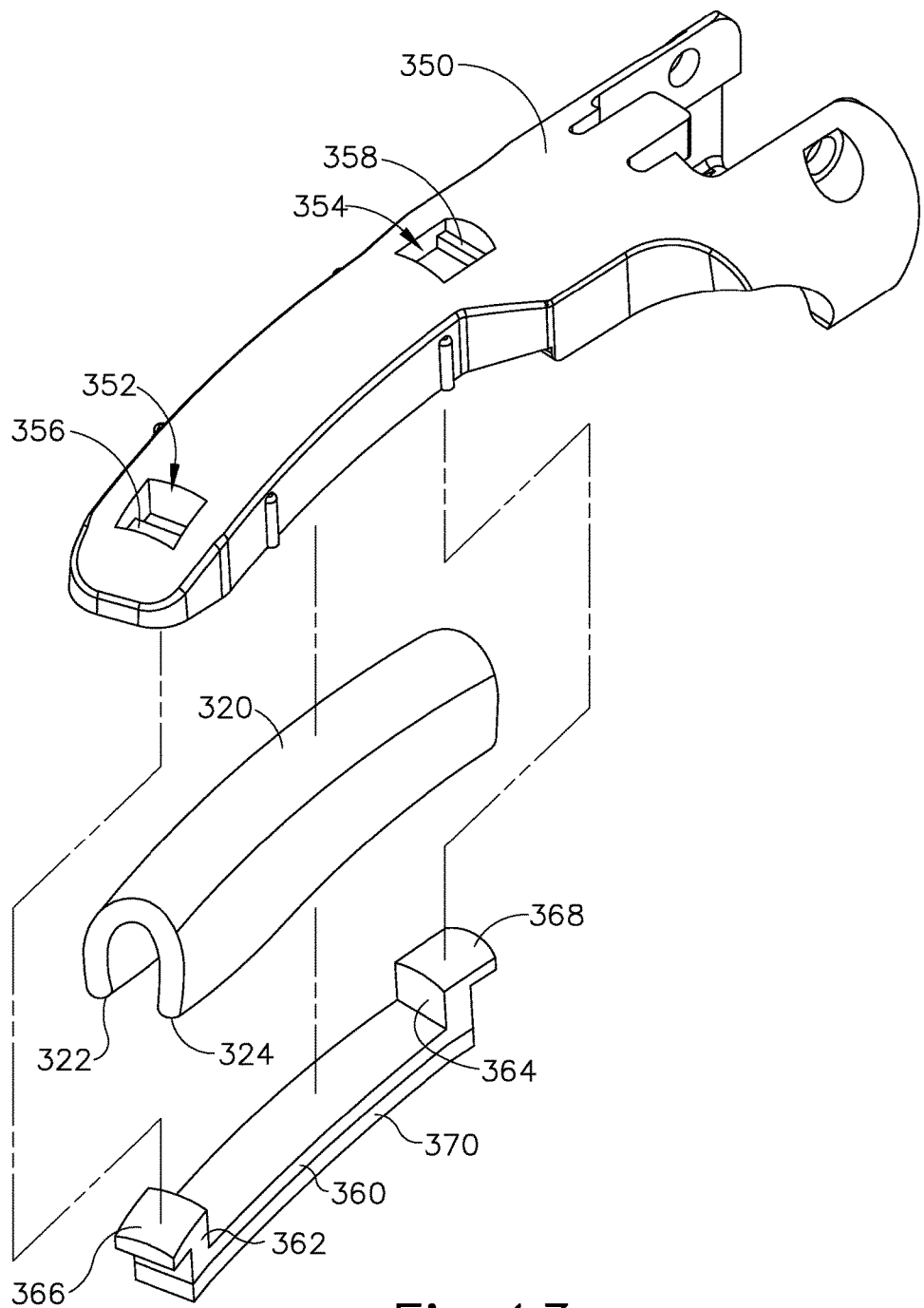
FIG. 13 depicts an exploded view of the clamp arm of FIG. 12.

FIGS. 12-13 show another exemplary clamp arm (350) that may be combined with pad (320). Clamp arm (350) of this example may also be used as a substitute for clamp arm (44). Clamp arm (350) of this example includes a pair of engagement channels (352, 354) that are longitudinally spaced apart from each other. Each engagement channel (352, 354) includes a respective internal shelf (356, 358). A retaining member (360) is configured to engage clamp arm (350). A clamp pad (370) is secured to the underside of retaining member (360). Retaining member (360) includes a pair of transversely extending arms (362, 364). Each arm (362, 364) includes a respective latch (366, 368). Arms (362, 364) are configured to be inserted through corresponding engagement channels (352, 354), such that latches (366, 368) engage corresponding shelves (356, 358) to secure retaining member (360) to clamp arm (350) in a snap fit.

Retaining member (360) is configured to secure pad (320) relative to clamp arm (350). In particular, pad (320) may be draped over retaining member (360); and retaining member (360) may then be secured to clamp arm (350) as described above such that pad (320) is captured between retaining member (360) and clamp arm (350). Free ends (322, 324) may again extend below clamp arm (300) and below clamp pad (310), such that pad (320) may engage a blade (42), in a manner similar to that shown in FIG. 11 and described above, when clamp arm (350) is in a closed position relative to blade (42). Thus, when pad (320) is saturated or otherwise wetted with a cooling fluid, pad (320) may quench or otherwise cool blade (42) when clamp arm (350) is in a closed position relative to blade (42). Other suitable ways in which a clamp arm may incorporate a cooling pad will be apparent to those of ordinary skill in the art in view of the teachings herein.

C. Exemplary Cooling Pad Insert for Inner Tube

Figure 14A:
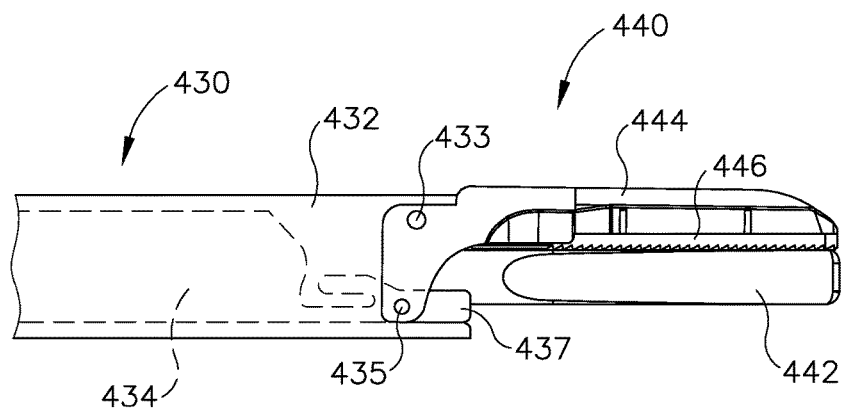
FIG. 14A depicts a side elevational view of another exemplary alternative end effector, in a closed configuration, with a cooling element spaced away from the ultrasonic blade.
Figure 14B:
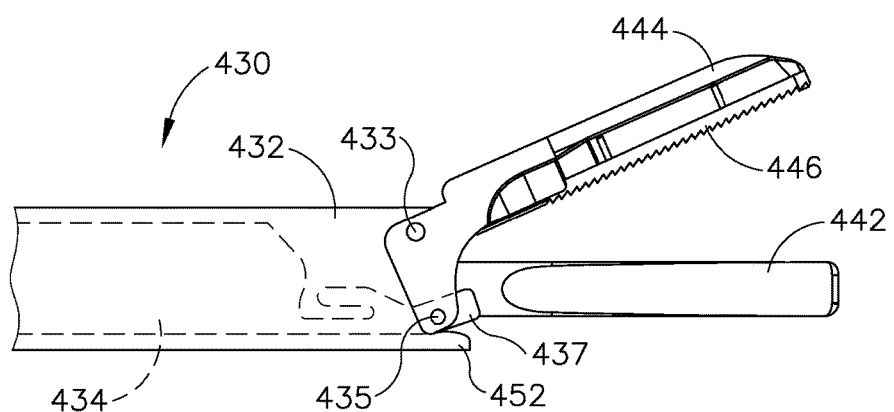
FIG. 14B depicts a side elevational view of the end effector of FIG. 14A, in an open configuration, with the cooling element in contact with the ultrasonic blade.
Figure 15:
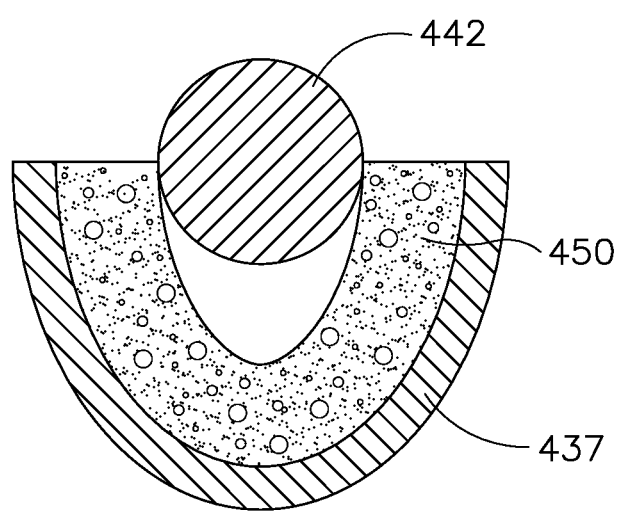
FIG. 15 depicts a cross-sectional end view of the cooling element of FIG. 14A in contact with the ultrasonic blade.

FIGS. 14A-15 show an exemplary alternative end effector (440) positioned at the distal end of an exemplary alternative shaft assembly (430). End effector (440) of this example is substantially similar to end effector (40) described above. In particular, end effector (440) includes an ultrasonic blade (442) and a pivoting clamp arm (444) with clamp pad (446). Shaft assembly (430) is substantially similar to shaft assembly (30) described above. In particular, shaft assembly (430) includes an outer sheath (432) and an inner tube (434). Outer sheath (432) is pivotably coupled with clamp arm (444) via a pin (433); while inner tube (434) is pivotably coupled with clamp arm (444) via a pin (435). Inner tube (434) translates relative to outer sheath (432) to selectively pivot clamp arm (444) toward (FIG. 14A) and away from (FIG. 14B) blade (442). Unlike inner tube (34), however, the distal end (437) of inner tube (434) of this example is resilient and includes an integral cooling pad (450). Unlike outer sheath (32), outer sheath (432) of this example includes a camming feature (452).

As best seen in FIG. 15, the distal end (437) of inner tube (434) is bent to form a "U" shape; and pad (450) also defines a "U" shape. This shape complements the configuration of blade (442). The distal end (437) of inner tube (434) and camming feature (452) of outer sheath (432) are configured such that camming feature (452) drives the distal end of inner tube (434) inwardly toward blade (442) when inner tube (434) travels distally, as shown in FIG. 14B. When inner tube (434) travels back proximally, the resilience of the distal end of inner tube (434) drives the distal end (437) of inner tube (434) outwardly. This inward/outward movement of the distal end of inner tube (434) provides selective engagement between pad (450) and blade (442). In some versions, distal end (437) comprises a plastic material that is insert molded with a metal material that forms the remainder of inner tube (434). In some other versions, distal end (437) is unitarily formed by a metal material that forms the remainder of inner tube (434). Other suitable ways in which distal end (437) may be formed will be apparent to those of ordinary skill in the art in view of the teachings herein. Also by way of example only, pad (450) may comprise a foam material. Various suitable material(s) that may be used to form pad (450) will be apparent to those of ordinary skill in the art in view of the teachings herein.

As with other pads described herein, pad (450) may be saturated or otherwise wetted with a cooling fluid (e.g., saline, etc.). Pad (450) may thus apply the cooling fluid to blade (442) when pad (450) engages blade (442), such that the saturated pad (450) quenches or otherwise cools blade (442) each time end effector (440) reaches an open configuration. End effector (440) may be dipped into a container holding saline or some other cooling fluid in order to saturate or otherwise wet pad (450). This may be done at the beginning of a surgical procedure and/or during a surgical procedure. In addition or in the alternative, pad (450) may absorb fluid from vapor emitted by tissue during a surgical procedure and/or other fluid from a surgical site. As yet another merely illustrative variation, a fluid conduit may be coupled with pad (450) to communicate fluid directly to pad (450) from a source external to the patient (e.g., a reservoir within a handle assembly, etc.). Other suitable ways in which pad (450) may be saturated or otherwise wetted will be apparent to those of ordinary skill in the art in view of the teachings herein.

III. Miscellaneous

In addition to or as an alternative to using fluid to reduce heat in a version of instrument (10, 100), one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features are described in U.S. Provisional Patent App. No. 61/908,920, the disclosure of which is incorporated by reference herein; and also in U.S. Pub. No. 2015/0148833, entitled "Shielding Features for Ultrasonic Blade of a Surgical Instrument," published May 28, 2015, the disclosure of which is incorporated by reference herein; and also in U.S. Pub. No. 2015/0148835, entitled "Sleeve Features for Ultrasonic Blade of a Surgical Instrument," published May 28, 2015, the disclosure of which is incorporated by reference herein. It should be understood that the teachings herein may be readily combined with the teachings of those references and the various other references cited herein. Other suitable examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement are described in U.S. Provisional Patent App. No. 61/908,920, the disclosure of which is incorporated by reference herein; and also in U.S. Pub. No. 2015/0148834, entitled "Ultrasonic Surgical Instrument with Staged Clamping," published May 28, 2015, the disclosure of which is incorporated by reference herein. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly includes an inner tube and an outer sheath, wherein one of the inner tube and the outer sheath is a translating member configured to translate relative to the body;
   (c) an end effector located at a distal end of the shaft assembly, wherein the end effector comprises:
      (i) an ultrasonic blade, wherein the ultrasonic blade is configured to vibrate at an ultrasonic frequency, and
      (ii) a clamp arm, wherein the clamp arm is configured to move toward and away from the ultrasonic blade in response to translation of the translating member; and
   (d) a wetting member, wherein the wetting member is positioned between the ultrasonic blade and the inner tube, wherein the wetting member is selectively movable by the translating member between a first position and a second position, wherein the wetting member is configured to be spaced away from the ultrasonic blade in the first position, wherein the wetting member is configured to contact the ultrasonic blade in the second position and thereby apply a cooling fluid to the ultrasonic blade.

2. The apparatus of claim 1, wherein the wetting member comprises a pad.

3. The apparatus of claim 2, wherein the pad comprises a foam material.

4. The apparatus of claim 1, further comprising a cam feature, wherein the cam feature is operable to selectively drive the wetting member toward the second position in response to movement of the cam feature.

5. The apparatus of claim 4, wherein the wetting member is resiliently biased toward the first position.

6. The apparatus of claim 4, wherein the wetting member comprises:
   (i) a pad saturated in the cooling fluid, and
   (ii) a beam, wherein the pad is mounted to the beam, wherein the cam feature is operable to deform the beam.

7. The apparatus of claim 6, wherein the wetting member further comprises a wicking feature, wherein the wicking feature is in communication with the pad, wherein the wicking feature runs along at least part of the length of the beam, wherein the wicking feature is operable to communicate fluid to the pad through a capillary action.

8. The apparatus of claim 1, wherein the translating member is operable to drive the wetting member toward the second position to thereby drive the wetting member into contact with the ultrasonic blade.

9. The apparatus of claim 1, wherein the translating member is the inner tube, wherein the inner tube is slidably disposed within the outer sheath.

10. The apparatus of claim 9, wherein the wetting member is mounted on a support member, wherein the support member is longitudinally fixed relative to the outer sheath.

11. The apparatus of claim 1, wherein the ultrasonic blade includes a clamping side configured to confront the clamp arm, and a non-clamping side arranged opposite of the clamping side, wherein the wetting member is positioned to contact the non-clamping side in the second position.

12. The apparatus of claim 1, wherein the wetting member is mounted on a support member, wherein the translating member includes an inwardly directed protrusion and is configured to translate relative to the support member to engage the protrusion with the support member and thereby drive the support member and the wetting member toward the ultrasonic blade and into the second position.

13. The apparatus of claim 12, wherein the support member extends longitudinally between the inner tube and the ultrasonic blade.

14. The apparatus of claim 12, wherein the support member includes a curved portion configured to align with and receive the protrusion of the tube to thereby enable the wetting member to assume the first position.

15. An apparatus comprising:
   (a) a body;
   (b) a shaft assembly extending distally from the body, wherein the shaft assembly comprises a translating member, wherein the translating member is operable to translate longitudinally relative to the body between a first position and a second position;
   (c) an end effector located at a distal end of the shaft assembly, wherein the end effector comprises:
      (i) an ultrasonic blade, wherein the ultrasonic blade is configured to vibrate at an ultrasonic frequency, and (ii) a clamp arm coupled with the translating member, wherein the clamp arm is configured to move away from the ultrasonic blade in response to movement of the translating member from the first position to the second position; and (d) a wetting member operatively coupled with the translating member, wherein the wetting member is configured to move toward and engage the ultrasonic blade and thereby apply a cooling fluid to the ultrasonic blade in response to movement of the translating member from the first position to the second position, wherein the wetting member is configured to disengage and move away from the ultrasonic blade in response to movement of the translating member from the second position to the first position, wherein the translating member is configured to drive the clamp arm away from the ultrasonic blade and simultaneously drive the wetting member toward the ultrasonic blade when the translating member moves from the first position to the second position.

16. The apparatus of claim 15, wherein the ultrasonic blade includes a clamping side configured to confront the clamp arm, and a non-clamping side arranged opposite of the clamping side, wherein the wetting member is configured to contact the non-clamping side when the translating member is in the second position.

17. An apparatus comprising:
(a) a body;
(b) a shaft extending distally from the body;
(c) an end effector located at a distal end of the shaft, wherein the end effector comprises:
  (i) an ultrasonic blade, wherein the ultrasonic blade is configured to vibrate at an ultrasonic frequency, wherein the ultrasonic blade includes a clamping side and an oppositely disposed non-clamping side, and
  (ii) a clamp arm, wherein the clamp arm is movable relative to the ultrasonic blade between an open position and a closed position for clamping tissue against the clamping side of the ultrasonic blade;
(d) a wetting member positioned alongside the non-clamping side of the ultrasonic blade, wherein the wetting member is movable between a first position in which the wetting member is positioned in non-contact relation with the ultrasonic blade, and a second position in which the wetting member contacts and applies a cooling fluid to the ultrasonic blade; and
(e) a user engageable feature operatively coupled with the clamp arm and the wetting member, wherein the user engageable feature is operable to actuate the clamp arm between the open and closed positions and simultaneously actuate the wetting member between the first and second positions.

18. The apparatus of claim 17, wherein the user engageable feature is operable to actuate the clamp arm to the open position and simultaneously actuate the wetting member to the second position.

* * * * *